(12) United States Patent  
Okamoto et al.

(10) Patent No.: US 9,028,688 B2
(45) Date of Patent: May 12, 2015

(54) INSTRUMENT FOR SEPARATING BLOOD AND APPARATUS FOR SEPARATING BLOOD

(75) Inventors: Ryusuke Okamoto, Shunan (JP); Katsuya Togawa, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 1059 days.

(21) Appl. No.: 11/994,055

(22) PCT Filed: Jun. 26, 2006

(86) PCT No.: PCT/JP2006/312705
§ 371 (c)(1),
(2), (4) Date: Dec. 27, 2007

(87) PCT Pub. No.: WO2007/000965
PCT Pub. Date: Jan. 4, 2007

(65) Prior Publication Data
US 2009/0050553 A1    Feb. 26, 2009

(30) Foreign Application Priority Data

Jun. 27, 2005    (JP) ................................ 2005-187119

(51) Int. Cl.
*B01D 29/00*    (2006.01)
*B01L 3/00*    (2006.01)
*G01N 33/49*    (2006.01)

(52) U.S. Cl.
CPC ....... *B01L 3/5635* (2013.01); *B01L 2300/0681* (2013.01); *G01N 33/491* (2013.01)

(58) Field of Classification Search
CPC ............................ B01L 13/563; B01L 13/5635
USPC ............ 210/233, 645, 472; 422/99, 101, 102, 422/103, 104
See application file for complete search history.

(56) References Cited

U.S. PATENT DOCUMENTS 4,126,558 A * 11/1978 Luceyk .......................... 210/429
4,244,379 A * 1/1981 Smith ............................ 600/579
(Continued)

FOREIGN PATENT DOCUMENTS

JP    05-093721 A    4/1993
JP    08-320317 A    12/1996
(Continued)

OTHER PUBLICATIONS

Extended European Search Report dated Aug. 5, 2010, as issued in European Application No. 06767322.8.

*Primary Examiner* — Tony G. Soohoo
*Assistant Examiner* — Peter Keyworth
(74) *Attorney, Agent, or Firm* — Sughrue Mion, PLLC

(57) ABSTRACT

Blood separation material which separates blood collected in a blood-sampling container, into blood cells and plasma or serum within a short period of time. An apparatus for separating blood with the blood separation material. An instrument for separating blood having a first hollow needle extending toward one end, a second hollow needle extending toward the other end, a tubular container with an inner space in which the blood flows, and a blood separation material. A container with a first channel for supplying blood into an inner space through which blood flows from the needlepoint of the first hollow needle into the inner space, a second channel for blood to flow out from the inner space toward the needlepoint of the second hollow needle, and a third channel which allows air to flow from the outer space toward the needlepoint of the first hollow needle.

9 Claims, 10 Drawing Sheets

(56) References Cited

U.S. PATENT DOCUMENTS

| | | | |
|---|---|---|---|
| 4,253,501 A * | 3/1981 | Ogle | 141/27 |
| 6,132,353 A | 10/2000 | Winkelman et al. | |
| 6,551,299 B2 * | 4/2003 | Miyoshi et al. | 604/403 |
| 2001/0045387 A1 * | 11/2001 | Amano et al. | 210/406 |
| 2003/0013205 A1 * | 1/2003 | Konrad | 436/177 |
| 2004/0254525 A1 * | 12/2004 | Uber et al. | 604/67 |
| 2005/0014273 A1 * | 1/2005 | Dahm et al. | 436/45 |
| 2005/0139547 A1 * | 6/2005 | Manoussakis et al. | 210/645 |
| 2006/0086750 A1 * | 4/2006 | Geyer et al. | 222/81 |

FOREIGN PATENT DOCUMENTS

| | | |
|---|---|---|
| JP | 08-320318 A | 12/1996 |
| JP | 2002-277357 A | 9/2002 |
| WO | 2005/066627 A1 | 7/2005 |

* cited by examiner

FIG. 2
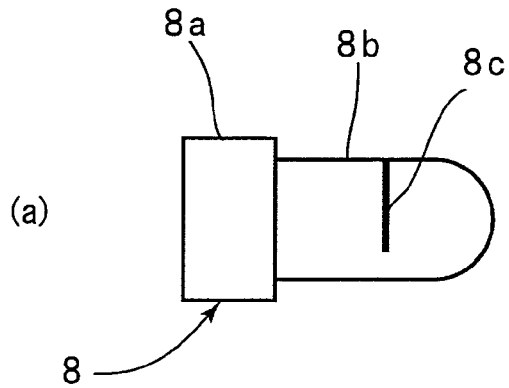
(a)
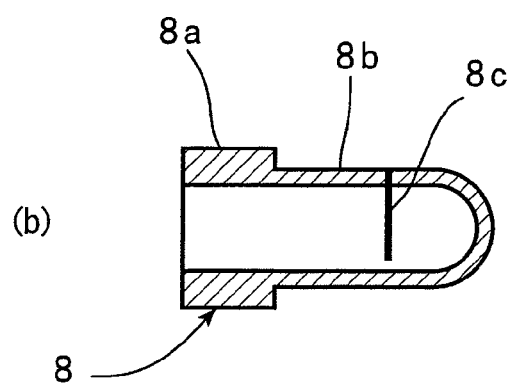
(b)
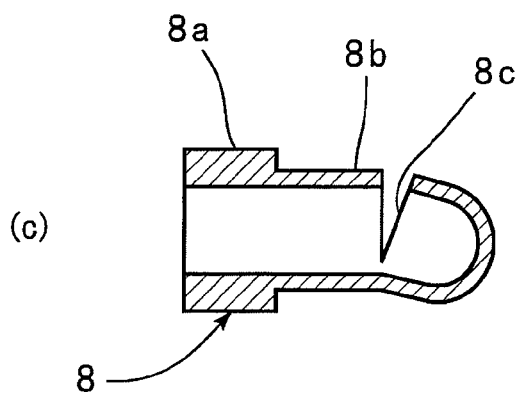
(c)

US 9,028,688 B2

INSTRUMENT FOR SEPARATING BLOOD AND APPARATUS FOR SEPARATING BLOOD

TECHNICAL FIELD

The present invention relates to an instrument for separating blood that is used for separating blood into blood cells and plasma or serum and, more specifically, to an instrument for separating blood which is able to easily separate blood collected in a blood-sampling container into blood cells and plasma or serum in a short time and an apparatus for separating blood provided with the instrument for separating blood.

BACKGROUND ART

Heretofore, a centrifugal separation method has been employed for removing blood cells from blood to obtain plasma or serum required for clinical laboratory. However, with the centrifugal separation method, operation in a coagulating process or a process of transferring supernatant plasma or serum after separation was complicated. In addition, it took a long time to obtain the result of examination, and a large and expensive centrifugal separator was necessary.

In order to solve the problems described above, various methods of separation and separators which are able to remove blood cells from blood and obtain plasma or serum required for clinical laboratory without using the centrifugal separator are proposed.

For example, an instrument for separating serum or plasma which is able to separate and collect the serum or plasma component from collected blood simultaneously or immediately after collection of blood sample is disclosed in Patent Document 1 shown below. Referring to FIG. 11, the instrument for separating serum or plasma disclosed in Patent Document 1 is described below.

As shown in vertical cross-section in FIG. 11, an instrument 101 for separating serum or plasma includes an external tube 102, a blood collection tube 103, a connecting member 104, and a separated liquid collection tube 105.

The external tube 102 has a cylindrical shape, and has an opening at a lower end 102a thereof. The external tube 102 has a blood collection needle 105 extending outward and inward from the center of an upper end surface 102b. The blood collection tube 103 includes a cylindrical container 106 and closing members 107, 108 attached to an upper end 106a and a lower end 106b of the cylindrical container 106. The closing members 107, 108 are formed of material which can be pierced through by a needle. Arranged in the interior of the blood collection tube 103 are a blood cell separation fiber material layer 109 on the side of the closing member 107 and a blood cell agglutination material layer 110 on the side of the closing member 108. The interior of the blood collection tube 103 is decompressed. In FIG. 11, the blood collection tube 103 is inserted into the external tube 102 from the opening at the lower end 102a of the external tube 102.

The separated liquid collection tube 105 includes an opening 105a at one end. The opening 105a is provided with a closing member 111 which allow a needle to be pierced therethrough. The interior of the separated liquid collection tube 105 is decompressed. The connecting member 104 is formed into a cylindrical shape, and has a partitioning wall 104a at the center thereof. The connecting member 104 includes a hollow needle 112 extending upward and downward from the center of the partitioning wall 104a.

When using the above-described instrument 101 for separating serum or plasma, the one end 105a of the blood collection needle 105 positioned outside the external tube 102 is inserted into a blood vessel. Simultaneously, the blood collection tube 103 is further inserted into the external tube 102, and the closing member 107 is pierced through by the other end 105b of the blood collection needle 105 opposite to the one end 105a. Consequently, blood flows into the interior of the blood collection tube 103 being decompressed. After a required amount of blood is flowed therein, the one end 105a of the blood collection needle 105 is pulled out from the blood vessel.

Subsequently, the closing member 108 of the blood collection tube 103 is pierced through by one end 112a of the hollow needle 112 of the connecting member 104. Simultaneously, the other end 112b of the hollow needle 111 of the connecting member 104 on the opposite side from the one end 112a pierces through the closing member 111 of the separated liquid collection tube 105. Consequently, blood flowed into the blood collection tube 103 is drawn into the separated liquid collection tube 105 by vacuum. At this time, the blood passes through the blood cell separation fiber material layer 109 and the blood cell agglutination material layer 110, and serum or plasma components are separated from blood. The separated serum or plasma components flow into the separated liquid collection tube 105 through the hollow needle 112.

Patent Document 1: JP-A-05-93721

DISCLOSURE OF THE INVENTION

According to the instrument 101 for separating serum or plasma disclosed in Patent Document 1, blood flows into the blood collection tube 103 by decompression of the interior of the blood collection tube 103. However, when the degree of decompression of the blood collection tube 103 is low, a required amount of blood may not quickly flow into the blood collection tube 103. In the instrument 101 for separating serum or plasma, the one end 105a of the blood collection needle 105 is inserted into a blood vessel to collect blood. In this case, for example, blood collected may reversely flow into the blood vessel and hence fiber contents or the like of the blood cell separation fiber material layer 108 in the blood collection tube 103 may flow into the blood vessel.

On the other hand, a method of providing a blood-sampling container, collecting blood in this container, and allowing the blood collected in the container to flow into the blood collection tube 103 is also conceivable. However, in this case as well, when the degree of decompression in the blood collection tube 103 is low, there is a case in which a required amount of blood cannot quickly flows into the blood collection tube 103. In addition, there are some possibilities that the pressure difference between the blood-sampling container and the interior of the blood collection tube 103 becomes almost zero as the blood flows into the blood collection tube 103, so that flow of blood into the blood collection tube 103 is stopped.

Under the circumstances, it is an object of the present invention to provide a blood separation material which is able to easily separate blood collected in a blood-sampling container into blood cells and plasma or serum in a short time and a apparatus for separating blood provided with the blood separation material.

The present invention is an instrument for separating blood used for separating blood into blood cells and plasma or serum and inspecting components in the plasma or the serum including: a first hollow needle extending toward one end; a second hollow needle extending toward the other end, which is the opposite side from the one end; a tubular container body arranged between the first and second hollow needles and having an inner space so as to allow passage of blood, and a blood separation material arranged in the inner space of the container body to separate blood into blood cells and plasma or serum, in which the container body includes a first channel which allows blood to flow from a needlepoint of the first hollow needle toward the inner space of the container body and flow into the inner space of the container body, a second channel which allows the blood to flow from the inner space toward a needlepoint of the second hollow needle and flow out from the inner space, and a third channel which may be brought into a state of allowing air to flow from an outer space toward the needlepoint of the first hollow needle.

According to a specific aspect of the instrument for separating blood in the present invention, a valve member is disposed in the third channel in a liquid-tight manner so as to allow air to flow from the outer space toward the needlepoint of the first hollow needle due to the pressure difference between the outer space and the needlepoint of the first hollow needle positioned on both sides of the valve member.

According to another specific aspect of the instrument for separating blood in the present invention, the valve member includes a notch, the notch opens and closes according to the presence or absence of the pressure difference, and opening of the notch allows air to flow from the outer space toward the needlepoint of the first hollow needle.

According to still another specific aspect of the instrument for separating blood in the present invention, a open cell foam material is arranged in the third channel in a liquid-tight manner, and the open cell foam material has a liquid-tight property and air permeability.

The apparatus for separating blood according to the present invention includes a blood-sampling container having an opening at least at one end and a closing member press-fitted into the opening for collecting blood therein and an instrument for separating blood configured according to the present invention.

According to a specific aspect of the apparatus for separating blood in the present invention, a sample storage container for storing separated plasma or serum, having an opening at least at one end and having a closing member press-fitted into the opening to keep the interior of the sample container in a decompressed state is further provided.

According to another specific aspect of the apparatus for separating blood in the present invention, the instrument for separating blood includes a cylindrical first holder extending from the container body toward one end of the container body and the first holder includes a first engaging portion projecting from an inner peripheral surface of the first holder so that the closing member of the blood-sampling container is engaged thereby when the closing member is pierced through by the first hollow needle.

According to still another specific aspect of the apparatus for separating blood in the present invention, the first holder includes a second engaging portion projecting from the inner peripheral surface of the first holder so that the closing member of the blood-sampling container is engaged thereby at a position before the closing member is pierced through by the first hollow needle.

According to still another specific aspect of the apparatus for separating blood in the present invention, the instrument for separating blood includes a cylindrical second holder extending from the container toward the other end of the container and the second holder includes the first engaging portion projecting from an inner peripheral surface of the second holder so that the closing member of the sample storage container is engaged thereby when the closing member is pierced through by the second hollow needle.

According to still another specific aspect of the apparatus for separating blood in the present invention, the second holder includes a second engaging portion projecting from the inner peripheral surface of the second holder so that the closing member of the sample storage container is engaged thereby at a position before the closing member is pierced through by the second hollow needle.

ADVANTAGES OF THE INVENTION

The instrument for separating blood according to the present invention is an instrument for separating blood used for separating blood into blood cells and plasma or serum and analyzing components in the plasma or the serum including: the first hollow needle extending toward one end; the second hollow needle extending toward the other end, which is the opposite side from the one end, the tubular container body arranged between the first and second hollow needles and having an inner space so as to allow passage of blood, and the blood separation material arranged in the inner space of the container for separating blood into blood cells and plasma or serum.

According to the present invention, the container body includes the first channel which allows blood to flow from the needlepoint of the first hollow needle toward the inner space and flow into the inner space, the second channel which allows the blood to flow from the inner space toward the needlepoint of the second hollow needle and flow out from the inner space, and a third channel which may be brought into a state of allowing air to flow from an outer space toward the needlepoint of the first hollow needle. Therefore, for example, when the needlepoint of the first hollow needle is inserted into the blood-sampling container which includes blood collected therein and is decompressed in the interior thereof, air moves from the outer space side toward the needlepoint through the third channel to allow air to flow from the needlepoint into the blood-sampling container. Therefore, even when blood flows into the inner space through the first channel, and hence the vacant volume in the blood-sampling container is increased, lowering of the pressure in the blood-sampling container is prevented, because air is flowed into the blood-sampling container. In addition, the blood in the blood-sampling container may flows out from the needlepoint of the second hollow needle through the first and second hollow needles.

In the case in which a valve member is arranged in the third channel in a liquid-tight manner so as to allow air to flow from the outer space toward the needlepoint of the first hollow needle due to the pressure difference between the outer space and the needlepoint of the first hollow needle on both sides of the valve member, for example, when the needlepoint of the first hollow needle is inserted into the blood-sampling container which includes blood collected therein and is decompressed in the interior thereof, air moves from the outer space side toward the needlepoint through the third channel to allow air to flow from the needlepoint into the blood-sampling container. In addition, even when the blood moves from the needlepoint of the first hollow needle toward the outer space through the third channel, the movement of the blood is stopped by the valve member. Therefore, the blood is prevented from flowing out to the outer space through the third channel.

In the case in which the valve member includes the notch, as the notch opens and closes according to the presence or absence of the pressure difference, opening of the notch allow air to flow from the outer space toward the needlepoint of the first hollow needle, the notch is closed when there is no pressure difference between the side of the outer space and the side of the needlepoint of the first hollow needle on both sides of the valve member, blood is more reliably prevented from flowing out to the outer space.

In the case in which the open cell foam material is arranged in the third channel in a liquid-tight manner and the open cell foam material has the liquid-tight property and air permeability, for example, when the needlepoint of the first hollow needle is inserted into the blood-sampling container including blood collected therein and being decompressed in the interior thereof, air moves from the outer space toward the needlepoint through the third channel and air reliably flows from the needlepoint into the blood-sampling container. Therefore, lowering of the pressure in the blood-sampling container is prevented further efficiently.

The apparatus for separating blood according to the present invention includes the blood-sampling container having the opening at least at one end and the closing member press-fitted into the opening for collecting blood therein and the instrument for separating blood configured according to the present invention. Therefore, when the closing member of the blood-sampling container is pierced through by the needlepoint of the first hollow needle, air moves from the outer space toward the needlepoint through the third channel, and hence air flows from the needlepoint into the blood-sampling container. Therefore, even when blood flows into the inner space through the first channel and the vacant volume in the blood-sampling container is increased, lowering of the pressure in the blood-sampling container is restrained. Therefore, the blood flows from the first channel to the inner space efficiently, and the plasma or the serum is separated and collected from the needlepoint of the second hollow needle through the second channel in a short time.

In a case of being provided the sample storage container having an opening at least at one end and having the closing member press-fitted into the opening so that decompression in the interior thereof is kept for storing separated plasma or serum therein, the blood in the blood-sampling container is vacuum sucked into the sample storage container when the closing member of the blood-sampling container is pierced through by the needlepoint of the first hollow needle, and the closing member of the sample storage container is pierced into the needlepoint of the second hollow needle. Since air flows from the third channel into the blood-sampling container even when the blood flows into the inner space through the first channel the vacant volume of the blood-sampling container is increased, lowering of the pressure in the blood-sampling container is prevented. Therefore, the pressure difference between the blood-sampling container and the sample storage container can hardly be reduced, blood is separated into blood cells and plasma or serum in a short time.

In a case that the instrument for separating blood includes the cylindrical first holder extending from the container body toward one end of the container body and the first holder includes a first engaging portion projecting from an inner peripheral surface of the first holder so that the closing member of the blood-sampling container is engaged thereby when the closing member is pierced through by the first hollow needle, the closing member of the blood-sampling container is easily pierced through by the first hollow needle. Furthermore, when separating blood, since the blood-sampling container is held by the instrument for separating blood, separation of the blood is safely achieved.

In a case that the first holder includes the second engaging portion projecting from the inner peripheral surface of the first holder so that the closing member of the blood-sampling container is engaged thereby at a position before the closing member is pierced through by the first hollow needle, the blood-sampling container is held by the instrument for separating blood in advance before separation of blood, and the closing member of the blood-sampling container is further easily pierced through by the first hollow needle.

In a case in which the instrument for separating blood includes the cylindrical second holder extending from the container toward the other end of the container and the second holder includes the first engaging portion projecting from an inner peripheral surface of the second holder so that the closing member of the sample storage container is engaged thereby when the closing member is pierced through by the second hollow needle, the closing member of the sample storage container is easily pierced through by the second hollow needle. Furthermore, when separating blood, since the sample storage container is held by the instrument for separating blood, separation of blood is safely achieved.

In a case that the second holder includes the second engaging portion projecting from the inner peripheral surface of the second holder so that the closing member of the sample storage container is engaged thereby at a position before the closing member is pierced through by the second hollow needle, the sample storage container is held by the instrument for separating blood in advance before separation of blood, and the closing member of the sample storage container is further easily pierced through by the second hollow needle.

BRIEF DESCRIPTION OF THE DRAWINGS

FIGS. 2(a) and (b) are a front view and a front cross section of a valve member of the instrument for separating blood according to the first embodiment of the present invention in an enlarged scale. FIG. 2(c) is a front cross section showing a state in which a notch of the valve member is opened.

EXPLANATION OF REFERENCE NUMERALS

Figure 1:
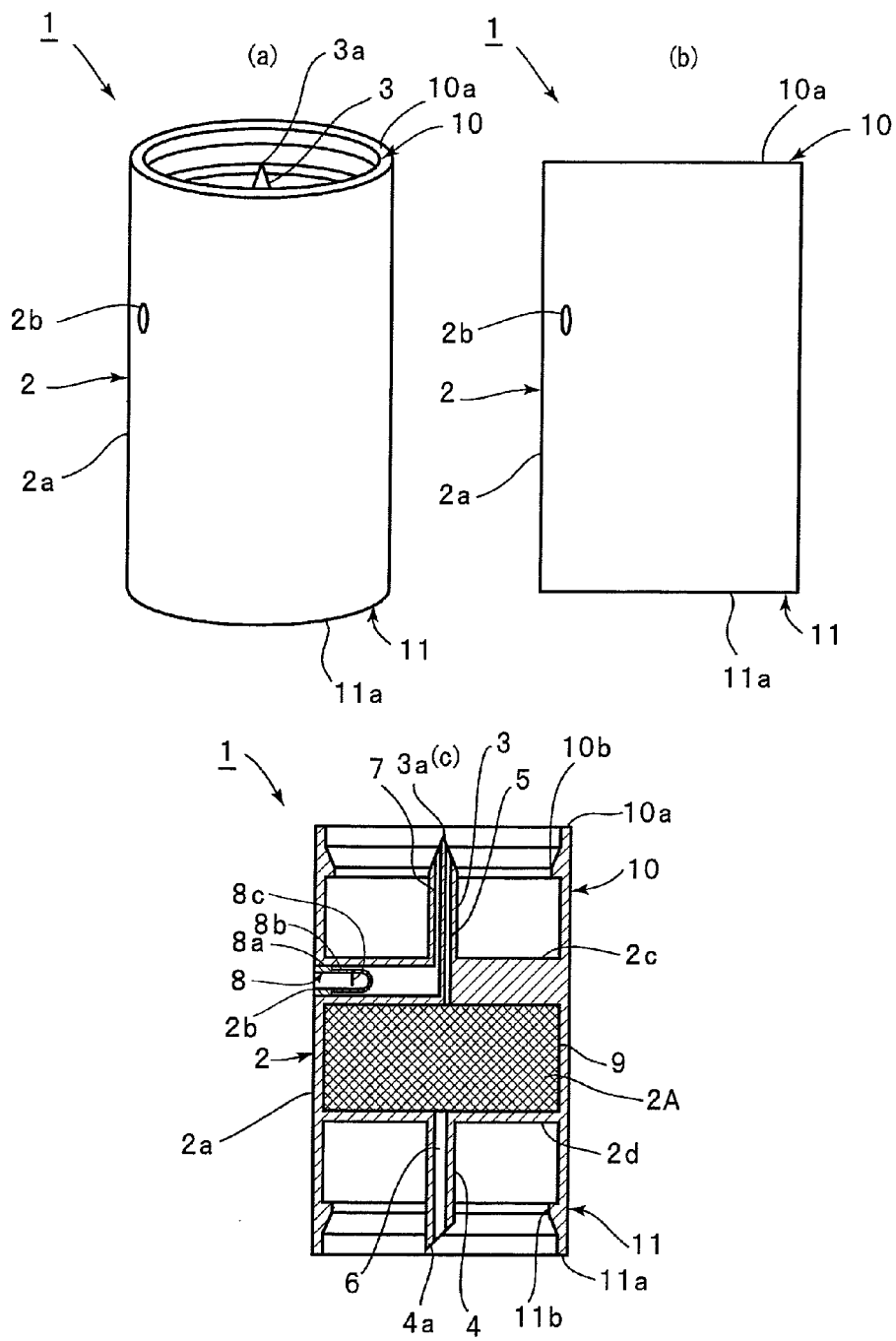
FIGS. 1(a) to (c) are a perspective view, a front view and a front cross section showing an instrument for separating blood according to a first embodiment of the present invention.

1: instrument for separating blood
2: container body
2a: side surface
2b: opening
2c: upper end surface
2d: lower end surface
2A: inner space
3: first hollow needle
3a: needlepoint
4: second hollow needle
4a: needlepoint
5: first channel
6: second channel
7: third channel
8: valve member
8a: thick portion
8b: main body portion
8c: notch
9: blood separation material
10: first holder
10a: upper end
10b: first engaging portion
11: second holder
11a: lower end
11b: second engaging portion
21: blood-sampling container
22: tubular container
22a: opening
23: closing member
23a: large diameter portion
23b: small diameter portion
23c, 23d: recess
31: sample storage container
41: instrument for separating blood
42: open cell foam material
51: instrument for separating blood
52: first holder
52a: upper end
52b: second engaging portion
52c: first engaging portion
52d: grip portion
55: blood-sampling container
56: cylindrical container
56a, 56b: both ends
61: instrument for separating blood
62: container
62a: lower end surface
62b: step
62A: inner space
63: blood separation material
64: blood cell trapping membrane
64a: hole
71: instrument for separating blood
72: container
72A: inner space
72a: lower end surface
72b: annular projection
73: blood separation material
74: channel closing member
74a: hole

BEST MODE FOR CARRYING OUT THE INVENTION

Referring now to the drawings, detailed embodiments of the present invention will be described so that the invention will be apparent.

Referring now to FIGS. 1(a) to (c), an instrument for separating blood according to a first embodiment of the present invention will be described. FIG. 1(a) is a perspective view showing an appearance of the instrument for separating blood, and FIG. 1(b) is a front view of the instrument for separating blood, and the FIG. 1(c) is a front cross section of the instrument for separating blood.

As shown in FIGS. 1(a) to (c), an apparatus 1 for separating blood includes a cylindrical container body 2. The container body 2 is not limited to a cylindrical shape, and may be of any tubular shape such as square tube shape. The shape of the container body 2 may be modified as needed corresponding to the shape of a blood-sampling container or a sample storage container described later.

Although the material for the container body 2 is not specifically limited, the same is made of synthetic resin or the like which can be injection-molded. The material of the container body 2 may be resin such as acrylonitril/butadiene/styrene (ABS), polyethylene terephthalate (PET), polycarbonate, polystyrene, polypropylene (PP), polyethylene (PE), nylon, or acryl.

As shown in FIG. 1(c), the container body 2 includes a first hollow needle 3 extending upward, which is one end of the instrument, and a second hollow needle 4 extending to downward, which is the other end on the opposite side from the one end. The container body 2 includes an inner space 2A between the first hollow needle 3 and the second hollow needle 4.

The container body 2 includes a first channel 5 extending from a needlepoint 3a of the first hollow needle 3 toward the inner space 2A for allowing blood to flow into the inner space 2A. The container body 2 includes a second channel 6 extending from the inner space 2A toward a needlepoint 4a of the second hollow needle 4 for allowing blood to flow from the inner space 2A. The container body 2 further includes a third channel 7 extending from the outer space toward the needlepoint 3a of the first hollow needle 3 which may be brought into a state of allowing passage of air.

The third channel 7 extends downward from the needlepoint 3a of the first hollow needle 3, is redirected sideward before reaching the inner space 2A, and reaches an opening 2b of a side surface 2a of the container body 2. Therefore, the needlepoint 3a and the outer space of the container body 2 are connected by the third channel 7.

A valve member 8 is inserted into the opening 2b of the container body 2. In other words, the valve member 8 is arranged so as to allow passage of air from the outer space toward the needlepoint 3a of the first hollow needle 3 due to the pressure difference between the outer space and the needlepoint 3a of the first hollow needle 3 positioned on both sides of the valve member 8. The valve member 8 is, for example, formed of a material having rubber resiliency, and has flexibility.

FIG. 2(a) is a front view of the valve member 8 in an enlarged scale, and FIG. 2(b) is a front cross section of the valve member 8 in an enlarged scale.

As shown in FIGS. 2(a) and (b), the valve member 8 has a substantially cylindrical shape, and has a thick portion 8a at one end. The outer diameter of the thick portion 8a is about a size so that the thick portion 8a can be press-fitted into the third channel 7, and is substantially the same as or slightly larger than the inner diameter of the opening 2b. A main body portion 8b continues from the thick portion 8a and the diameter of the main body portion 8b is relatively smaller than the diameter of the thick portion 8a. The main body portion 8b is formed with a notch 8c. The notch 8c is easily formed by cutting the valve member 8, for example, made of a material having rubber resiliency with a cutter or the like.

In this embodiment, the notch 8c is formed so as to extend in the direction orthogonal to the longitudinal direction of the valve member 8, and the valve member 8 is configured so that the notch 8c opens and closes according to the presence or absence of the pressure difference. The valve member 8 is configured so as to allow passage of air from the outer space toward the needlepoint 3a of the first hollow needle 3 when the notch 8c is opened.

The material for the valve member 8 is not specifically limited as long as it is formed of a material having rubber resiliency at room temperature. As a material for the valve member 8, for example, natural rubber, isoprene rubber, butyl rubber, urethane and thermoplastic elastomer are exemplified.

Returning back to FIG. 1(c), the valve member 8 is inserted in such a manner that the thick portion 8a is positioned on the side of the side surface 2a. The valve member 8 is inserted and press-fitted into the opening 2b from the opposite side to the thick portion 8a, that is, from a closed portion of the main body portion 8b. The outer peripheral surface of the thick portion 8a is in tight contact with the inner peripheral surface of the third channel 7 in a liquid-tight manner.

On the other hand, the notch 8c is positioned at a portion of the valve member 8 fixed to the third channel 7, that is, on the side of the needlepoint 3a of the first hollow needle with respect to the thick portion 8a. The third channel 7 extends inward from the opening 2b. The notch 8c extends in the direction orthogonal to the direction in which the third channel 7 is formed at a portion of the third channel 7 which extends inwardly.

The inner space 2A of the container body 2 is provided with a blood separation material 9 arranged therein.

The material which constitutes the blood separation material 9 is not specifically limited and, for example, polyethylene, polypropylene, polyethylene terephthalate, polybutylene terephthalate, polystyrene, polyvinyl acetate, urethane, acryl, rayon and glass are exemplified.

As the blood separation material, for example, accumulated extra fine fibers, foam or sintered body having continuous air bubbles, hollow fiber membrane, porous membrane, porous particles, film having a plurality of grooves and/or holes are exemplified. However, it is not limited to the examples shown above as long as it is substantially able to separate blood into blood cells and plasma or serum. Separation may be done by trapping blood cell components in the interior of the filter, or by the difference of transfer velocity between the blood cell component and plasma or serum component.

The blood separation material includes asymmetry filters and symmetry filters. The asymmetry filter is a generic name of filters having a configuration in which the hole diameter is reduced from the blood incoming side to the outgoing side. Other types of blood separation materials are generically referred to as symmetry filters.

The symmetry filter from among these blood separation materials preferably has an average hole diameter from 1 μm to 10 μm and, more preferably, from 2 μm to 8 μm. When the average hole diameter is smaller than 1 μm, the red blood cells may be hemolyzed and, when it is larger than 10 μm, separation of the blood cells and plasma or serum may be remarkably degraded.

The asymmetry filter from among these blood separation materials preferably has an average hole diameter from 0.01 μm to 10 μm and, more preferably, from 0.1 μm to 6 μm. When the average hole diameter is smaller than 0.01 μm, the blood cell component clogs the holes and hence separation cannot be achieved, or may be hemolyzed, and when the average hole diameter is larger than 10 μm, separation of the blood cell and plasma or serum may be remarkably deteriorated.

When the blood separation material is formed of accumulated extra fine fibers, it is preferably formed by accumulating fibers having an average fiber diameter in the range from 0.5 to 3.0 μm. When the average fiber diameter is smaller than 0.5 μm, hemolysis occurs easily when separating blood. When the average fiber diameter is larger than 3.0 μm, it is necessary to form the blood separation material at high density in order to separate the blood cells and plasma or serum, and the amount of fibers to be used is increased, and hence the cost is also increased. In order to enhance the effect of blood separation, the average fiber diameter is preferably in the range from 0.5 to 2.5 μm.

The average density of the blood separation material when packed in the container is preferable in the range from 0.1 to 0.5 g/cm$^3$. When the average density is lower than 0.1 g/cm$^3$, separation of blood cannot be performed effectively, and hence the amount of plasma or serum obtained may be reduced. When the average density is higher than 0.5 g/cm$^3$, the load to the red blood cells is increased, and hence hemolysis occurs easily. In order to separate blood further efficiently, the average density is preferably in the range from 0.15 to 0.40 g/cm$^3$.

It is also possible to use a combination of the symmetry filter and the asymmetry filter as the blood separation material.

The blood separation material may have a property to adsorb components in blood. In this case, a surface treatment may be applied to the blood separation material for restraining or controlling the adsorption of the components in the blood. The surface treatment agent is not specifically limited, but may be polyether or silicon contained lubricant, hydrophilic high molecular such as polyvinyl alcohol or polyvinyl pyrrolidone, natural hydrophilic high molecular, or high molecular surface active agents. The surface of the blood separation material may be applied with chemical processing using oxidizing agent, plasma treatment or the like to provide hydrophilic property. In contrast, it may be applied with water repellent treatment by a hydrophobic silicon or fluorinated surface treatment agent.

The instrument 1 for separating blood includes a cylindrical first holder 10 extending upward from an upper end surface 2c of the container body 2. An annular first engaging portion 10b is formed on the inner peripheral surface of the first holder 10 near an upper end 10a thereof so as to extend inwardly from the inner peripheral surface of the first holder 10. The instrument 1 for separating blood includes a cylindrical second holder 11 extending downward from an lower end surface 2d of the container body 2. An annular first engaging portion 11b is formed on the inner peripheral surface of the second holder 11 near a lower end 11a thereof so as to extend inwardly from the inner peripheral surface of the second holder 11.

In this embodiment, the container body 2, and the first and second holders 10, 11 are integrally formed. However, they may be formed of different members. The shape of the first engaging portion is not specifically limited, and may be, for example, a dot shape in addition to the annular shape as described above. The first and second holders 10, 11 are formed of, for example, the same material as the container described above, although not specifically limited.

Figure 3:
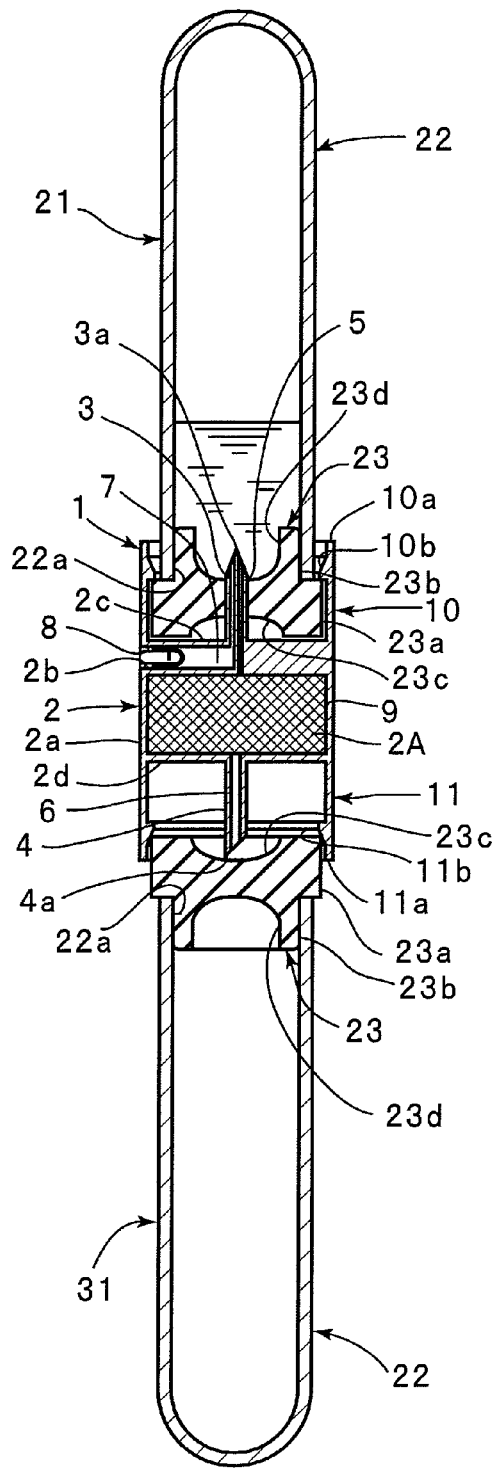
FIG. 3 is an explanatory drawing showing how to use the instrument for separating blood according to the first embodiment of the present invention and is a vertical cross section showing a state immediately before blood is flowed into a container.
Figure 4:
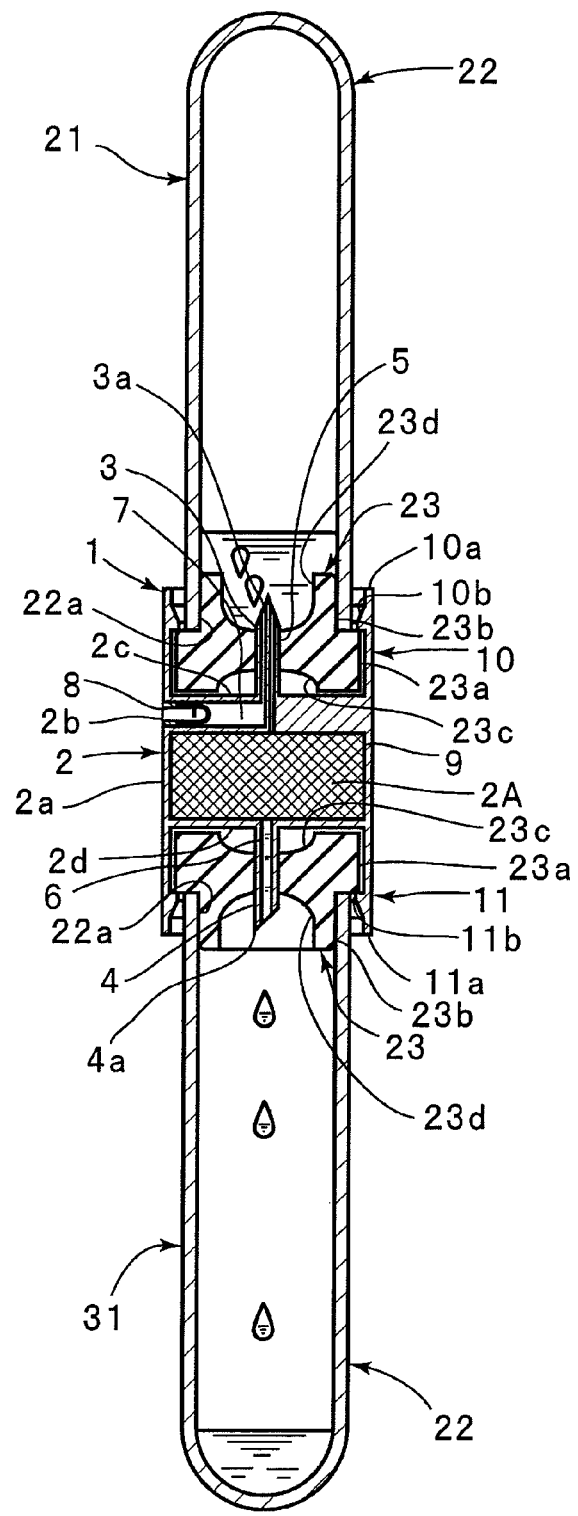
FIG. 4 is an explanatory drawing showing how to use the instrument for separating blood according to the first embodiment of the present invention and is a vertical cross section showing a state in which blood flowed into the container is in the course of being separated.
Figure 5:
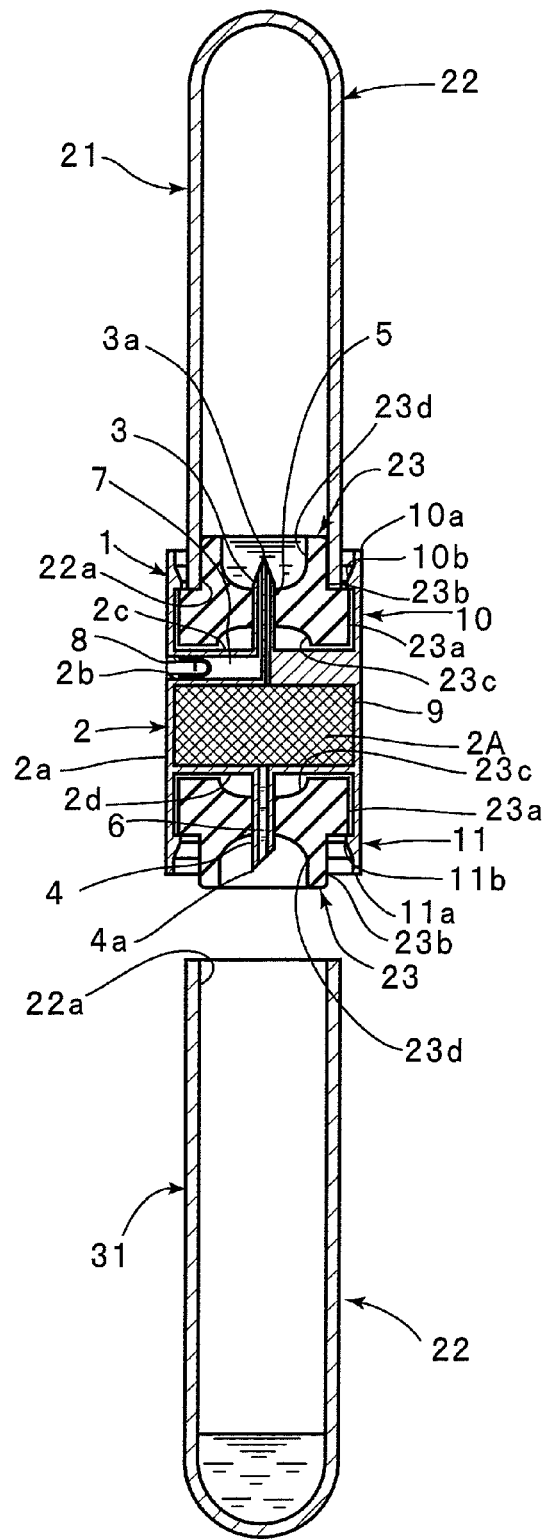
FIG. 5 is an explanatory drawing showing how to use the instrument for separating blood according to the first embodiment of the present invention and is a vertical cross section showing a state in which separated plasma or serum is taken out.

Referring to FIG. 3 to FIG. 5, how to use the instrument 1 for separating blood described above will be described.

FIG. 3 is a vertical cross section showing a state immediately before blood is flowed into the container body 2. FIG. 4 is a vertical cross section showing a state in which the blood flowed into the container body 2 is in the course of being separated. FIG. 5 is a vertical cross section showing a state of taking separated plasma or serum out.

As shown in FIG. 3, a blood-sampling container 21 in which blood is collected, and a sample storage container 31 in which separated plasma or serum is stored are prepared.

The blood-sampling container 21 includes a bottomed tubular container 22 formed, for example, of glass. The tubular container 22 has an opening 22a on one side thereof. A closing member 23 is press-fitted into the opening 22a so as to hermetically seal the interior thereof. The closing member 23 includes a large diameter portion 23a and a small diameter portion 23b having a smaller diameter than the large diameter portion 23a. The closing member 23 is provided with recesses 23c, 23d at the center of the outer and inner surfaces thereof respectively so as to facilitate piercing by a blood collection needle or syringe. The small diameter portion 23b is press-fitted into the opening 22a, and the opening 22a is hermetically sealed by the closing member 23. The interior of the blood-sampling container 21 before use is decompressed. For example, when blood is collected into the blood-sampling container 21 by removing the closing member 23 once, the interior of the blood-sampling container 21 does not have to be decompressed.

The sample storage container 31 is configured in the same manner as the blood-sampling container 21 described above. Therefore, the same reference numerals are given and the description is omitted. In the interior of the sample storage container 31 is decompressed. The reason why the interior of the sample storage container 31 is decompressed is to vacuum suck and filter blood as described later.

The closing member 23 is not specifically limited as long as it is formed of materials which have an airtight property and can be pierced through by the first and second hollow needles 3, 4. The closing member 23 is composed, for example, of rubber resilient material. The rubber resilient material as such may be natural rubber, butyl rubber, thermoplastic elastomer, and the like.

The degree of decompression in the interior of the sample storage container 31 is not specifically limited. However, a range from 2 to 90 kPa is preferable and a range from 20 to 60 kPa is more preferable. When the degree of decompression is too low, separation of blood may not be achieved quickly, and when the degree of decompression is too high, a pressure is exerted to the red blood cells, and hemolysis may be resulted.

When separating blood, the blood is firstly collected in the above-described blood-sampling container 21. The method of collecting blood is not specifically limited.

However, one end of a blood collecting needle is inserted into a blood vessel and the other end thereof pieces through the closing member 23 using the blood-sampling needle for example, so that blood is flowed into the blood-sampling container 21. As shown in FIG. 3, after having collected blood into the blood-sampling container 21, the blood-sampling container 21 is inserted into the upper end 10a of the first holder 10 from the side of the closing member 23. In other words, the closing member 23 of the blood-sampling container 21 is pierced through by the needlepoint 3a of the first hollow needle 3. When the closing member 23 pierces through the needlepoint 3a and reaches the inner space of the blood-sampling container 21, the outer surface of the closing member 23 comes into abutment with the upper end surface 2c. At this time, a stepped surface between the large diameter portion 23a and the small diameter portion 23b of the closing member 23 is engaged by the first engaging portion 10b, so that the blood-sampling container 21 is held by the apparatus for separating blood 1.

Subsequently, as shown in FIG. 4, the sample storage container 31 is inserted into the lower end 11a of the second holder 11 from the closing member 23 side. In other words, the closing member 23 is pierced through by the needlepoint 4a of the second hollow needle 4. When the needlepoint 4a pierces through the closing member 23 and reaches the inner space of the sample storage container 31, the outer surface of the closing member 23 comes into abutment with the lower end surface 2d. At this time, the stepped surface between the large diameter portion 23a and small diameter portion 23b of the closing member 23 is engaged by the first engaging portion 10b, so that the sample storage container 31 is held by the apparatus for separating blood 1.

In this embodiment, the relation of the pressure when separation is started is P3>P1>P2 or P3≅P1>P2, where P1 is the pressure in the blood-sampling container 21, P2 is the pressure in the sample storage container 31, and P3 is the pressure in the outer space, that is, atmospheric pressure is satisfied. Therefore, when the needlepoint 4a pierces through the closing member 23, blood is vacuum sucked by the sample storage container 31 whose interior is decompressed. The blood in the sample storage container 31 passes through the first channel 5, and reaches the blood separation material 9. In the blood separation material 9, when blood passes therethrough, plasma or serum moves relatively faster than blood cells. The plasma or serum which has moved relatively faster passes through the second channel 6 and flows out into the sample storage container 31.

When the relation of the pressure described above is P3>P1>P2, the notch 8c of the valve member 8 is opened due to the pressure difference between the outer space and the needlepoint 3a of the first hollow needle 3 positioned on both sides of the valve member 8, and air flows into the blood-sampling container 21 through the third channel 7. Consequently, the relation of the pressure will be P3≅P1>P2.

In other words, as shown in the front cross section in FIG. 2(c), the notch 8c of the valve member 8 is opened due to the pressure difference between the outer space and the needlepoint 3a of the first hollow needle 3 on both sides of the valve member. When the notch 8c is opened, air flows into the blood-sampling container 21 through the third channel 7. When the pressure difference between the interior of the blood-sampling container 21 and the outer space becomes almost zero, the notch 8c of the valve member 8 having rubber resiliency is opened and is restored to the state shown in FIG. 2(b). Therefore, the pressure difference between the interior of the blood-sampling container 21 and the outer space becomes almost zero, and hence blood is prevented from flowing into the outer space through the notch 8c of the valve member 8 even when the blood is flowed into the third channel 7 from the needlepoint 3a.

On the other hand, when the relation of the pressure described above is P3=P1>P2, blood passes through the first and second channels 5, 6 and blood is flowed out from the needlepoint 4a of the second hollow needle 4. However, the vacant volume in the interior of the blood-sampling container 21 increases as the blood is separated. When the vacant volume is increased, the pressure in the blood-sampling container 21 is decreased. Therefore, the relation of the pressure becomes P3>P1>P2. In this case as well, air flows into the blood-sampling container 21 through the third channel 7, and the relation of the pressure becomes P3≅P1>P2.

As described above, in this embodiment, increase of the vacant volume in the blood-sampling container 21 and decrease of the pressure in the blood-sampling container 21 are prevented. In other words, the pressure P1 in the blood-sampling container 21 and the pressure P2 in the sample storage container 31 become substantially the same while blood is separated, and hence separation of blood is prevented from becoming slow or stopped. Therefore, with the instrument 1 for separating blood, blood is separated into blood cells and plasma or serum easily in a short time.

As shown in FIG. 5, after having terminated the separation of the blood, the instrument 1 for separating blood is removed from the sample storage container 31. At this time, since the stepped surface of the closing member 23 between the large diameter portion 23a and the small diameter portion 23b is engaged by the first engaging portion 11b of the second holder 11, the instrument 1 for separating blood is removed easily together with the closing member 23.

Separated plasma or serum is taken out easily from the opening 22a of the sample storage container 31 using a dropping pipette or by inclining the sample storage container 31.

Figure 6:
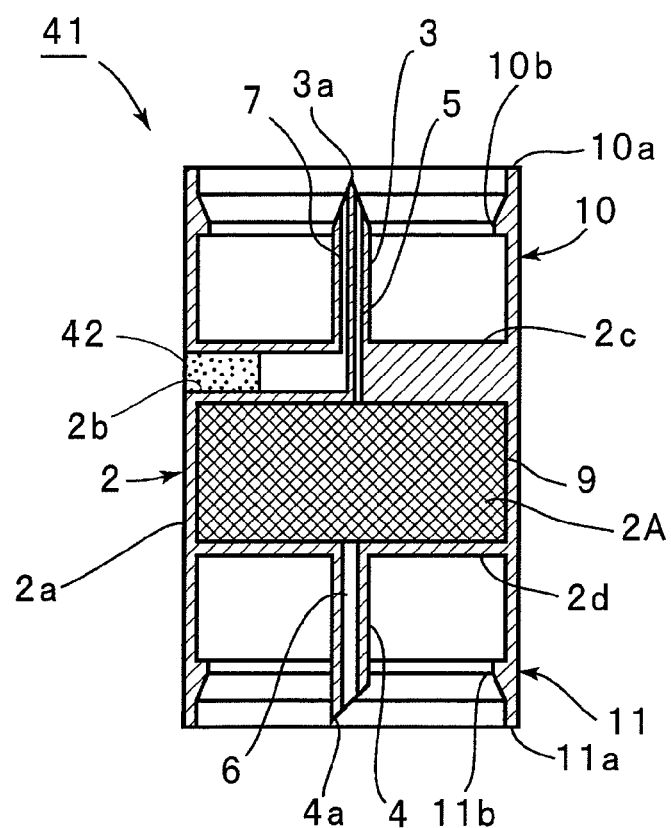
FIG. 6 is a front cross section showing the instrument for separating blood according to a second embodiment of the present invention.

FIG. 6 is a front cross section of an instrument for separating blood according to a second embodiment of the present invention.

In the case of the instrument 1 for separating blood according to the first embodiment, the valve member 8 is inserted into the third channel 7. However, in the case of an instrument 41 for separating blood, a open cell foam material 42 is inserted instead of the valve member 8.

The outer diameter of the open cell foam material 42 is about a size so that the same can be press-fitted into the third channel 7, which is substantially the same or slightly larger than the inner diameter of the opening 2b. The open cell foam material 42 is inserted and press-fitted into the opening 2b. The outer peripheral surface of the open cell foam material 42 is closely in contact with the inner peripheral surface of the third channel 7 in a liquid tight manner. The open cell foam material 42 has a liquid tight property and air permeability.

In the instrument 41 for separating blood, air passes through the third channel 7 from the outer space toward the needlepoint 3a of the first hollow needle 3, and air flows into the blood-sampling container 21. Therefore, since lowering of the pressure in the blood-sampling container 21 is restrained in the instrument 41 for separating blood, blood is separated into blood cells and plasma or serum easily in a short time.

The open cell foam material 42 is not specifically limited as long as it is configured to have liquid-tight property and air permeability. The material which constitutes the open cell foam material 42 includes urethane, polyvinyl alcohol (PVA) and polyethylene (PE). The open cell foam material 42 also includes porous member such as nonwoven fabric.

Figure 7:
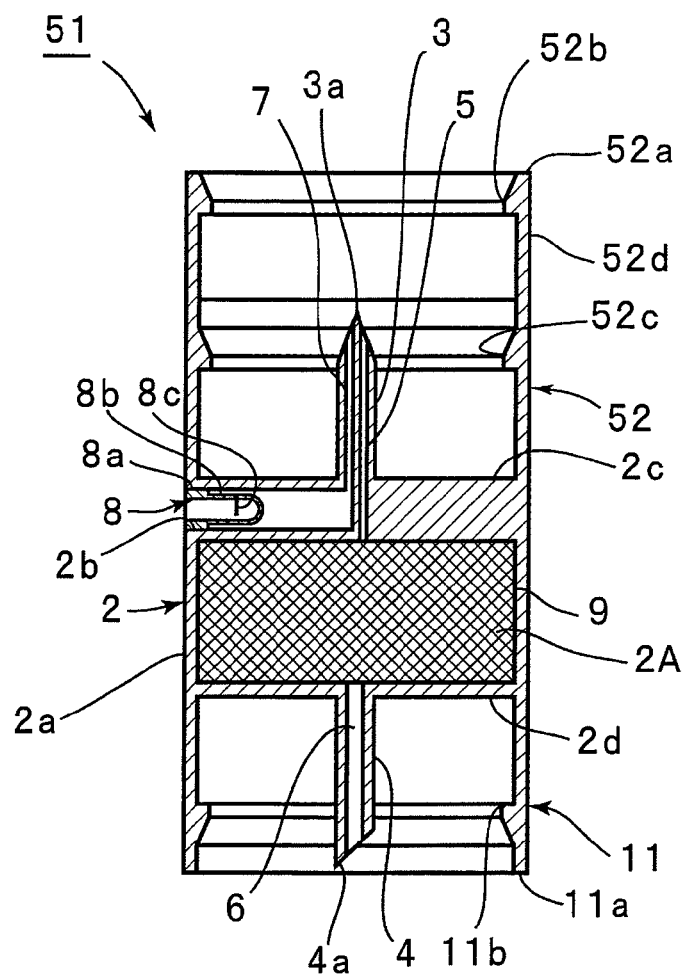
FIG. 7 is a front cross section showing the instrument for separating blood according to a third embodiment of the present invention.

FIG. 7 is a front cross section of an instrument for separating blood according to a third embodiment of the present invention.

The instrument 1 for separating blood in the first embodiment and an instrument 51 for separating blood shown in FIG. 7 are different in structure of the first holder. In the instrument 51 for separating blood, when the closing member 23 of the blood-sampling container 21 is positioned before the first hollow needle 3 pierces therethrough, or when the first hollow needle 3 pierces through the closing member 23, the blood-sampling container 21 is held by the instrument 1 for separating blood as will be described later.

The instrument 51 for separating blood includes a cylindrical first holder 52 extending upward from the upper end surface 2c of the container body 2. A second engaging portion 52b is formed on the inner peripheral surface of the first holder 52 near an upper end 52a there. In addition, a first engaging portion 52c is formed on the inner peripheral surface of the cylindrical first holder 52 near the center thereof. In other words, the first holder 52 has a grip portion 52d for griping the blood-sampling container between the first and second engaging portions 52b, 52c. In this embodiment, the container body 2 and the first holder 52 are integrally formed.

FIG. 8(a) is a front cross section showing a state in which the blood-sampling container is held by the instrument 51 for separating blood at a position before the first hollow needle 3 pierces through the closing member 23 of the blood-sampling container. FIG. 8(b) is a front cross section showing a state in which the blood-sampling container is held by the instrument 51 for separating blood when the first hollow needle 3 pierces through the closing member 23 of the blood-sampling container.

Figure 8:
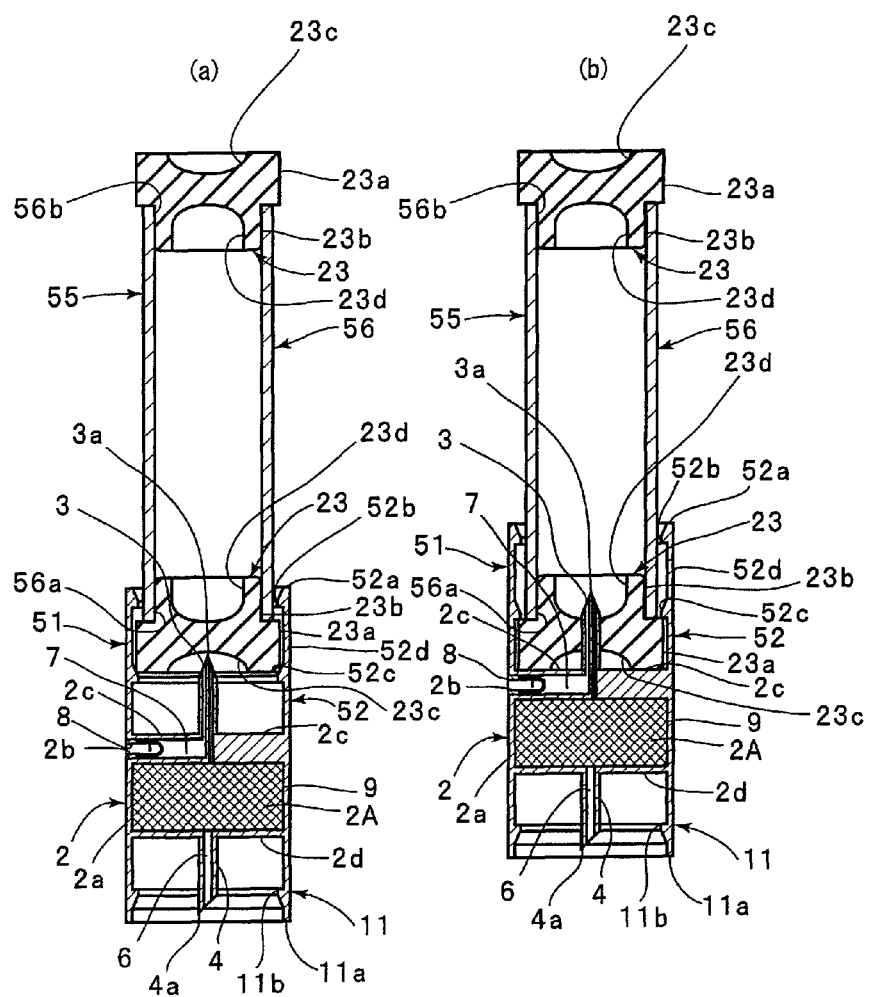
FIGS. 8(a) and (b) are front cross sections showing a state in which the blood-sampling container is held by the instrument for separating blood according to the third embodiment of the present invention.

The blood-sampling container 55 shown in FIG. 8 is different from the blood-sampling container 21 described above in the shape of the tubular container 22. The blood-sampling container 55 has a cylindrical container 56 opened at both ends 56a, 56b. Then, the closing member 23 described above is press-fitted into the openings of the both ends 56a, 56b. In this manner, the blood-sampling container and the sample storage container may be opened at both ends and the closing members may be press-fitted into the openings. The shapes of the blood-sampling container and the sample storage container may be changed as needed to a shape such as a square tube shape.

As shown in FIG. 8(a), in the instrument 51 for separating blood, the large diameter portion 23a of the closing member 23 is arranged between the second and first engaging portions 52b, 52c at a position before the needlepoint 3a pierces through the closing member 23, and the stepped surface between the large diameter portion 23a and the small diameter portion 23b is engaged by the second engaging portion 52b. Accordingly, the instrument 51 for separating blood is able to hold the blood-sampling container 55.

As shown in FIG. 8(b), in the instrument 51 for separating blood, when the blood-sampling container 55 is further inserted from the upper end 52a of the first holder 52, the needlepoint 3a pierces through the closing member 23. When the needlepoint 3a reaches the inner space of the blood-sampling container 55, the outer surface of the closing member 23 comes into abutment with the upper end surface 2c. At this time, the stepped surface of the closing member 23 between the large diameter portion 23a and the small diameter portion is engaged by the first engaging portion 52c, and the blood-sampling container 55 is held by the instrument 51 for separating blood.

In the instrument 51 for separating blood, the second holder 11 may be configured in the same manner as the first holder 52 described above. In other words, the second holder may be configured in such a manner that the sample storage container 31 is held by the instrument 1 for separating blood when the closing member 23 of the sample storage container 31 is at the position before the second hollow needle 4 pierces through the closing member 23, or when the second hollow needle 4 pierces through the closing member 23.

Figure 9:
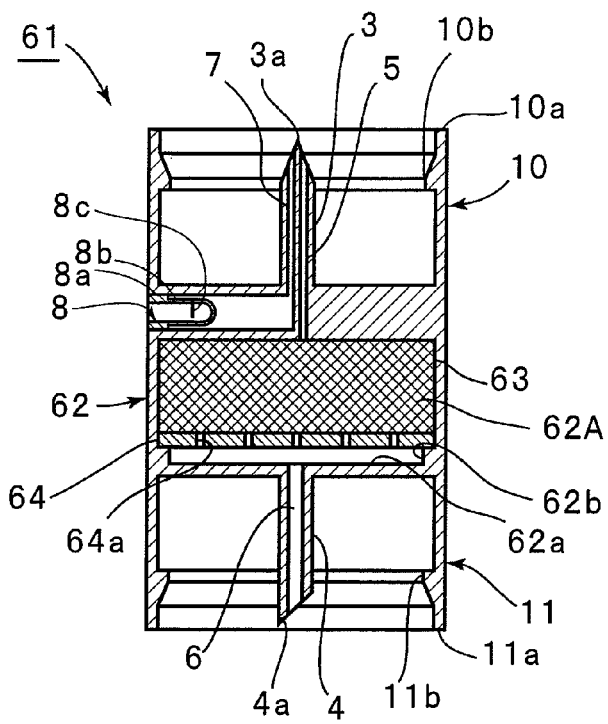
FIG. 9 is a front cross section showing the instrument for separating blood according to a fourth embodiment of the present invention.

FIG. 9 shows a front cross section of an instrument for separating blood according to a fourth embodiment of the present invention.

In an instrument 61 for separating blood shown in FIG. 9, of which container body is different in shape from the container body 2 of the instrument 1 of the first embodiment and, in particular, of which inner space is different in shape from the inner space 2A of the instrument 1 of the first embodiment. In the instrument 61 for separating blood, a blood separation material 63 and a blood cell trapping membrane 64 are arranged in an inner space 62A of a container 62.

The instrument 61 for separating blood has the cylindrical container 62. The container 62 includes the first hollow needle 3 and the second hollow needle 4, and the inner space 62A between the first hollow needle 3 and the second hollow needle 4. The container 62 includes the first to third channels 5 to 7.

The inner peripheral surface of the container 62 above a lower end surface 62a, that is, the inner peripheral surface of a part which continues from the inner space 62A to the second channel 6 is formed with an annular step 62b so as to extend inward.

The blood cell trapping membrane 64 is arranged in the inner space 62A so as to be supported by the annular step 62b. The blood separation material 63 is arranged in the inner space 62A above the blood cell trapping membrane 64, and an upper surface of the blood cell trapping membrane 64 is in contact with a lower surface of the blood separation material 63.

The blood cell trapping membrane 64 is formed of a membrane having a number of holes 64a so as not to allow passage of blood cells but to allow passage of plasma or serum. It may be a filter member other than the membrane as a matter of course.

In the instrument 61 for separating blood, plasma or serum moves faster than blood cells because of the presence of the blood separation material 63. The plasma or serum which has moved relatively faster passes through the holes 64a of the blood cell trapping membrane 64. The blood cells moved at a lower velocity than plasma or serum does not pass through the blood cell trapping membrane 64 even when they reaches the blood cell trapping membrane 64. Therefore, the blood cells are not mixed with the plasma or serum stored in the sample storage container 31 or the like. Therefore, a reliable result of examination is presented from the plasma or serum obtained thereby.

The material which constitutes the blood cell trapping membrane 64 is not specifically limited and includes, for example, polyvinylidene difluoride, polytetrafluoroethylene, acetylcellulose, nitrocellulose, polycarbonate, polyethylene terephthalate, polyethylene, polypropylene, glass fiber, borosilicate, vinyl chloride, silver. The material of the blood cell trapping filter is not limited as long as it has a property which is able to prevent passage of the red blood cells. The materials having such property include polyvinylidene difluoride, polytetrafluoroethylene, acetylcellulose, nitrocellulose, polycarbonate, polyethylene terephthalate, polyethylene, polypropylene, glass fiber, borosilicate, vinyl chloride, silver.

When the blood cell trapping membrane is composed of a porous substance, passage of plasma or serum is achieved. As a porous substance which constitutes the blood cell trapping membrane is not specifically limited as long as it has holes having a diameter which is able to prevent passage of the red blood cells. In order to prevent passage of red blood cells, the hole diameter is preferably 1 μm or smaller. When the hole diameter is too small, the holes may be clogged by protein component in the blood. Therefore, the hole diameter is preferably 0.01 μm or larger. In order to prevent passage of the red blood cells further effectively, the hole diameter is preferably in a range from 0.05 μm to 1 μm inclusive.

In order to increase filtering velocity, the surface of the blood cell trapping membrane may be applied with hydrophilic treatment. The method of the hydrophilic treatment includes plasma treatment and coating with hydrophilic high molecular. However, it is not limited thereto, and other methods may be employed.

Figure 10:
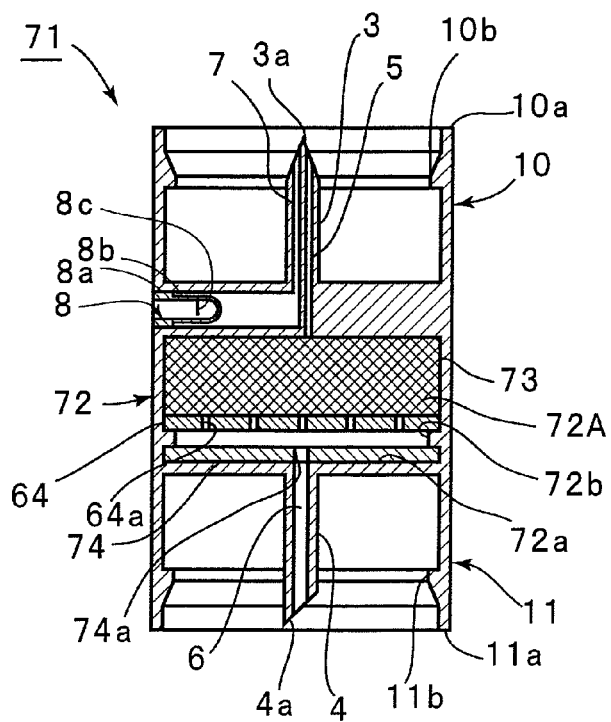
FIG. 10 is a front cross section showing the instrument for separating blood according to a fifth embodiment of the present invention.
Figure 11:
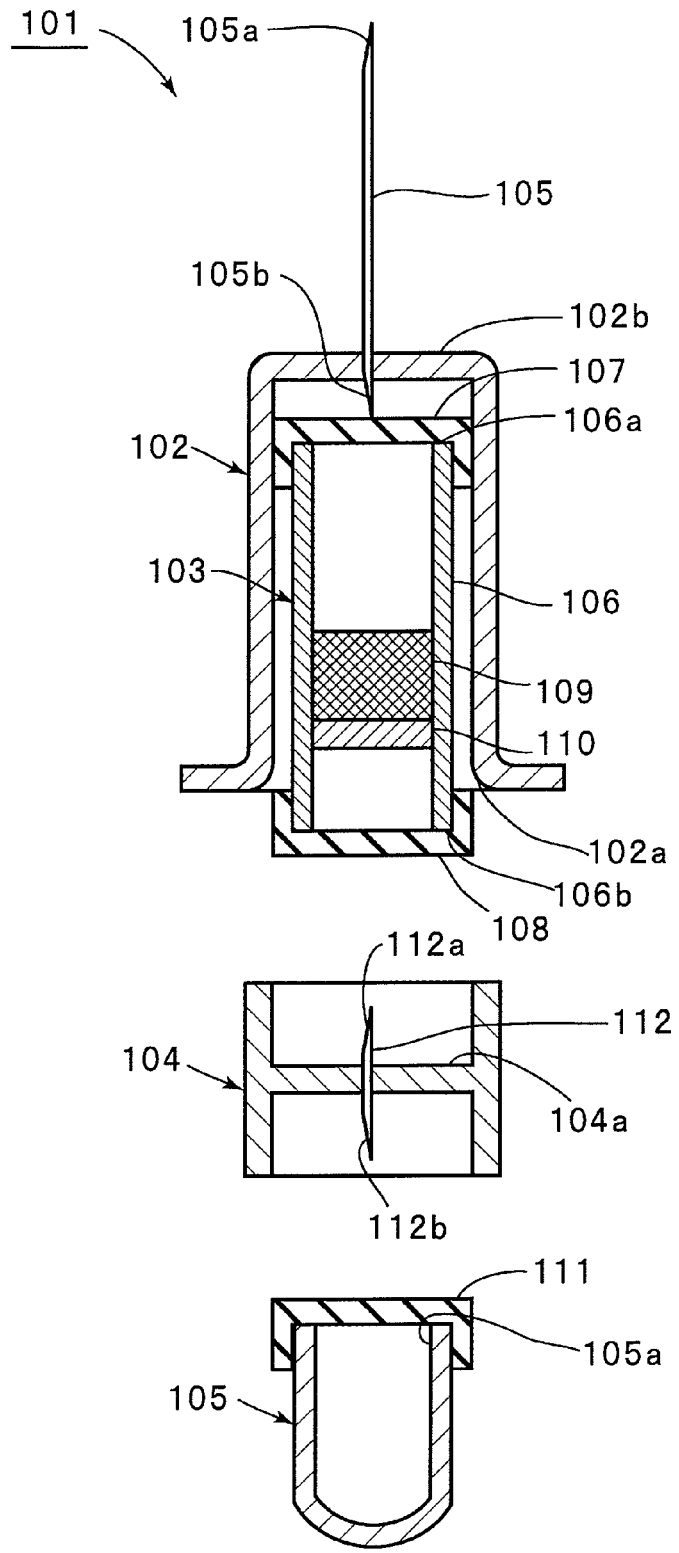
FIG. 11 is a front cross section schematically showing an instrument for separating blood in the related art.

FIG. 10 is a front cross section of an instrument for separating blood according to a fifth embodiment of the present invention.

In an instrument 71 for separating blood shown in FIG. 10, of which container body is different in shape from the container body 2 of the instrument 1 of the first embodiment and, in particular, of which inner space is different in shape from the inner space 2A of the instrument 1 of the first embodiment. Furthermore, in the instrument 71 for separating blood, a blood separation material 73, the blood cell trapping membrane 64 and a channel closing member 74 are arranged in an inner space 72A of a container 72.

The instrument 71 for separating blood includes the cylindrical container 72. The container 72 includes the first hollow needle 3 and the second hollow needle 4, and includes the inner space 72A between the first hollow needle 3 and the second hollow needle 4. The container 72 includes the first to third channels 5 to 7.

The container 72 includes an annular projection 72b extending inwardly from the inner peripheral surface slightly above a lower end surface 72a.

The blood cell trapping membrane 64 is arranged in the inner space 72A so as to be supported by the annular projection 72b. The blood separation material 73 is arranged in the inner space 72A above the blood cell trapping membrane 64, and an upper surface of the blood cell trapping membrane 64 is in contact with a lower surface of the blood separation material 73.

The channel closing member 74 is arranged so as to be held between the lower end surface 72a of the container 72 and the annular projection 72b. The channel closing member 74 includes a hole 74a at the center thereof, and the hole 74a continues to the second channel 6.

The channel closing member 74 is composed of a material which swells when it comes into contact with liquid component such as water content. The channel closing member 74 gradually swells when it comes into contact with plasma or serum, and closes the channel when the plasma or serum to be stored has passed therethrough. More specifically, the channel closing member 74 swells after the plasma or serum which had moved relatively faster in the blood separation material 73 has passed through the channel portion where the channel closing member 74 is arranged. In other words, it swells to close the hole 74a of the channel closing member 74 so that the channel is closed.

Even when the plasma or serum is left untouched for a long time after having stored the plasma or serum in the sample storage container 31 or the like, components in red blood cells generated by hemolysis do not drop downward since the channel is closed. When the channel is closed, the movement of the blood components driven by the pressure difference is also stopped below the channel closing member 74. Therefore, the components in red blood cells are not mixed with the plasma or serum. Therefore, when the obtained plasma or serum is inspected, a highly reliable result of examination is presented.

As the material for the channel closing member 74, for example, resin having a hydrophilic functional group in its molecular framework and a property which is able to absorb water of at least the same quantity as its own weight is exemplified. As specific examples of the material which constitutes the channel closing member 74, there are poly acrylic alkali metal chlorine contained resin or a copolymer thereof and crosslinked form thereof, polyacrylamide contained resin or a copolymer thereof and a crosslinked form thereof, poly N-vinyl acetamide contained resin or a copolymer thereof and a crosslinked form thereof, silicon contained resin or a copolymer thereof and a crosslinked form thereof, polyvinyl ether contained resin or a copolymer thereof and a crosslinked form thereof, polyalkylene oxide contained resin and a copolymer thereof and a crosslinked form thereof, polyvinyl alcohol, polyvinyl pyrrolidone or a copolymer thereof and a crosslinked form thereof.

The channel closing member may be of powder form or particle form, may be those formed into a film or sheet, or may be those obtained by adding in the form of paste, slurry or solution and drying out the same.

The channel closing member 74 swells by itself by being in contact with plasma or serum and closes the channel. Therefore, the quantity of required channel closing member differs depending on the volume of the channel to be closed, and the swelling ratio and the swelling velocity of the channel closing member. Therefore, an optimal quantity of the channel closing member is calculated from the volume of the channel to be closed, and the swelling ratio and the swelling velocity of the channel closing member.

The volume of the channel to be closed is set in a range which achieves absorption of water content in blood and prevents the quantity of sample to be collected from being reduced. When the volume of the channel is increased, the quantity of the channel closing member for closing the same is increased as well. Therefore, the quantity of sample to be collected may be reduced.

Therefore, the volume of the channel to be closed is preferably in a range from 0.005 to 1.0 cm$^3$. The volume of the channel closing member is preferably in a range of 5 to 95% with respect to the volume of the channel to be closed. When the volume of the channel closing member is smaller than 5% with respect to the volume of the channel to be closed, it takes a long time until the channel is closed, and hence the components leaked from red blood cells due to hemolysis may be mixed with separated plasma or serum. When the volume of the channel closing member is larger than 95% with respect to the volume of the channel to be closed, the channel may be closed before the entire part of plasma or serum is collected, and hence the efficiency of collection of the plasma or serum may be lowered.

What is claimed is:

1. An instrument for separating blood into blood cells and plasma or serum and analyzing components in the plasma or the serum comprising:
    a blood-sampling container having an opening at least at one end and a closing member having a large diameter portion, a small diameter portion and a stepped surface between the large diameter portion and the small diameter portion and press-fitted into the opening for collecting blood therein,
    a first hollow needle extending toward one end of the instrument; a second hollow needle extending toward the other end of the instrument, which is the opposite side from the one end; a tubular container body arranged between the first and second hollow needles and having an inner space so as to allow passage of blood; and a blood separation material arranged in the inner space of the container body to separate blood into blood cells and plasma or serum, wherein the blood separation material has an average hole diameter of from 2 μm to 8 μm;
    wherein the container body includes a first channel which allows blood to flow from a needlepoint of the first hollow needle toward the inner space of the container body and flow into the inner space of the container body, a second channel which allows the blood to flow from the inner space toward a needlepoint of the second hollow needle and flow out from the inner space, and a third channel which adjoins and extends downward from the needlepoint of the first hollow needle and an end of the third channel redirected sideways reaches an opening of a side surface of the container body allowing outside air to enter the third channel and flow toward the needlepoint of the first hollow needle to prevent pressure lowering in the blood sampling container when the first hollow needle is attached to the blood sampling container, and wherein the third channel is formed within the container body; and
    wherein the instrument for separating blood comprises a cylindrical first holder extending from said container body toward one end of the container body and the first holder includes a first engaging portion projecting from an inner peripheral surface of the first holder, which can be opposite to the stepped surface so that the stepped surface is engaged by the first engaging portion when the closing member is pierced through by the first hollow needle, and wherein the first holder includes a second engaging portion projecting from the inner peripheral surface of the first holder so that the closing member of the blood-sampling container is engaged thereby at a position before the closing member is pierced through by the first hollow needle.

2. The instrument for separating blood according to claim 1, wherein a valve member is disposed in the third channel in a liquid-tight manner so as to allow air to flow from the outer space toward the needlepoint of the first hollow needle due to the pressure difference between the outer space and the needlepoint of the first hollow needle positioned on both sides of the valve member.

3. The instrument for separating blood according to claim 2, wherein the valve member includes a notch, the notch opens and closes according to the presence or absence of the pressure difference, and opening of the notch allow air to flow from the outer space toward the needlepoint of the first hollow needle.

4. The instrument for separating blood according to claim 3, which is further applied to a sample storage container for storing separated plasma or serum comprising a closing member; and
    the instrument for separating blood further comprising a cylindrical second holder extending from the container body of the instrument toward the other end of the container body and the second holder includes a first engaging portion projecting from an inner peripheral surface of the second holder so that the closing member of the sample storage container is engaged thereby when the closing member is pierced through the second hollow needle.

5. The instrument for separating blood according to claim 4, wherein the second holder includes a second engaging portion projecting from the inner peripheral surface of the second holder so that the closing member of the sample storage container is engaged thereby at a position before the closing member is pierced through by the second hollow needle.

6. The instrument for separating blood according to claim 1, wherein an open cell foam material is arranged in the third channel in a liquid-tight manner, and the open foam cell material has a liquid-tight property and air permeability.

7. The instruments for separating blood according to claim 6, which is further applied to a sample storage container for storing separated plasma or serum comprising a closing member; and
    the instrument for separating blood further comprising a cylindrical second holder extending from the container body of the instrument toward the other end of the container body and the second holder includes a first engaging portion projecting from an inner peripheral surface of the second holder so that the closing member of the sample storage container is engaged thereby when the closing member is pierced through by the second hollow needle.

8. The instrument for separating blood according to claim 7, wherein the second holder includes a second engaging portion projecting from the inner peripheral surface of the second holder so that the closing member of the sample storage container is engaged thereby at a position before the closing member is pierced through by the second hollow needle.

9. An instrument for separating blood into blood cells and plasma or serum and analyzing components in the plasma or the serum comprising:
    a blood-sampling container having an opening at least at one end and a closing member having a large diameter portion, a small diameter portion, a stepped surface between the large diameter portion and the small diameter portion and press-fitted into the opening for collecting blood therein,
    a first hollow needle extending toward one end of the instrument; a second hollow needle extending toward the other end of the instrument, which is the opposite side from the one end; a tubular container body arranged between the first and second hollow needles and having an inner space so as to allow passage of blood; and a blood separation material arranged in the inner space of the container body to separate blood into blood cells and plasma or serum, wherein the blood separation material has an average hole diameter of from 2 μm to 8 μm:
    wherein the container body includes a first channel which allows blood to flow from a needlepoint of the first hollow needle toward the inner space of the container body and flow into the inner space of the container body, a second channel which allows the blood to flow from the inner space toward a needlepoint of the second hollow needle and flow out from the inner space, and a third channel which adjoins and extends downward from the needlepoint of the first hollow needle and an end of the third channel redirected sideways reaches an opening of a side surface of the container body allowing outside air to enter the third channel and flow toward the needlepoint of the first hollow needle to prevent pressure lowering in the blood sampling container when the first hollow needle is attached to the blood sampling container, wherein the third channel is formed within the container body;
wherein the instrument for separating blood comprises a cylindrical first holder extending from said container body toward one end of the container body and the first holder includes a first engaging portion projecting from an inner peripheral surface of the first holder, which can be opposite to the stepped surface so that the stepped surface is engaged by the first engaging portion when the closing member is pierced through by the first hollow needle;
wherein the instrument for separating blood comprises a sample storage container for storing separated plasma or serum, having an opening at least at one end and having a closing member press-fitted into the opening to keep the interior of the sample storage container in a decompressed state; and
wherein the instrument for separating blood comprises a cylindrical second holder extending from the container toward the other end of the container and the second holder includes a first engaging portion projecting from an inner peripheral surface of the second holder so that the closing member of the sample storage container is engaged thereby when the closing member is pierced through by the second hollow needle, wherein the second holder includes a second engaging portion projecting from the inner peripheral surface of the second holder so that the closing member of the sample storage container is engaged thereby at a position before the closing member is pierced through by the second hollow needle.

\* \* \* \* \*